United States Patent [19]
Batchelder et al.

[11] Patent Number: 5,648,268
[45] Date of Patent: Jul. 15, 1997

[54] RADIONUCLIDE EXCHANGE DETECTION OF ULTRA TRACE IONIC IMPURITIES IN WATER

[75] Inventors: John Samuel Batchelder, Somers; Philip Charles Danby Hobbs, Briarcliff Manor; Miro Plechaty, Katonah, all of N.Y.; Keith Randal Pope, Danbury, Conn.

[73] Assignee: IBM Corporation, Armonk, N.Y.

[21] Appl. No.: 349,842

[22] Filed: Dec. 6, 1994

[51] Int. Cl.$^6$ .................................................. G01N 23/00
[52] U.S. Cl. ........................ 436/57; 210/662; 210/682; 250/391; 376/157; 436/73; 436/77; 436/79; 436/80; 436/84; 436/161; 134/2
[58] Field of Search ...................... 210/656, 660, 210/662, 682, 688; 250/391; 376/157; 436/57, 161, 73, 80, 84, 79, 77; 134/2

[56] References Cited

U.S. PATENT DOCUMENTS

| | | |
|---|---|---|
| 3,117,842 | 1/1964 | Dewey, II . |
| 3,614,443 | 10/1971 | Horwitz et al. . |
| 3,657,541 | 4/1972 | Deutsch et al. . |
| 3,929,410 | 12/1975 | Schloss . |
| 4,351,643 | 9/1982 | Govindaraju . |
| 4,430,226 | 2/1984 | Hegde et al. . |
| 4,464,343 | 8/1984 | Hitchcock et al. . |
| 4,563,337 | 1/1986 | Kim . |
| 4,704,245 | 11/1987 | Asakura et al. . |
| 4,770,783 | 9/1988 | Gustavsson et al. . |
| 4,772,548 | 9/1988 | Stavrianpoulos . |
| 4,787,980 | 11/1988 | Ackermann et al. . |
| 4,861,445 | 8/1989 | Champetier . |
| 4,975,378 | 12/1990 | Banarjee . |
| 5,001,072 | 3/1991 | Olson . |
| 5,023,449 | 6/1991 | Holenka et al. . |
| 5,047,507 | 9/1991 | Buchegger et al. . |
| 5,049,280 | 9/1991 | Raymond et al. . |
| 5,073,268 | 12/1991 | Saito et al. . |
| 5,078,842 | 1/1992 | Wood et al. . |
| 5,122,268 | 6/1992 | Burack et al. . |

OTHER PUBLICATIONS

Iyengar (1987) "Radiochemical Separations for Inorganic Trace Elements in Some Biological Reference Materials, Foods, Tissues and Body–Fluids", *Journal of Radioanalytical and Nuclear Chemistry* 110, No. 2, 503–517.

Schuhmacher, et al. (1977) "A Half Automated, Non Time Consuming Radiochemical Separation Scheme for Determination of 25 Trace Elements in Biological Specimens", *Journal of Radioanalytical Chemistry* 37, 503–509.

Akaiwa (1984) "Ion Exchange Based on Complexation using a Chelating Agent–Loaded Resin and its Application to Preconcentration and Radioactivation Analysis of Trace Chalcophile Elements", *Journal of Radioanalytical and Nuclear Chemistry* 84, 165–175.

Krishnan, et al. (1975) "Sodium Removal by Hydrated Antimony Pentoxide in Neutron Activation Analysis", *Radiochem. Radioanal. Letters* 20, 279–287.

Hadzistelios, et al. (1969) "Radiochemical Microdetermination of Manganese Strontium and Barium by Ion–Exchange", *Pergamon Press* 16, 337–344.

Sato, et al. (1991) "Photoexcited Processes for Semiconductors II: Dry Cleaning and Dry Etching", *Fujitsu Sci. Tech. J.* 27, 317–328.

Holynska (1974) "The use of Chelating Ion Exchanger in Conjunction with Radioisotope X–ray Spectrometry for Determination of Trace Amounts of Metals in Water", *Radiochem. Radioanal. Letters* 17, 313–324.

(List continued on next page.)

*Primary Examiner*—Jill Warden
*Assistant Examiner*—Jan M. Ludlow
*Attorney, Agent, or Firm*—Scully, Scott, Murphy & Presser

[57] ABSTRACT

The present invention is directed to an analytic method for detecting trace elements in fluid solution. A cation exchange resin is packed with a radiolabelled exchange material having certain characteristics and replaces the trace element ions in the fluid which becomes labelled. The label is subsequently detected using sensitive and well known radiation detection methods.

22 Claims, 3 Drawing Sheets

OTHER PUBLICATIONS

Mishima, et al. (1989) "Particle–Free Wafer Cleaning and Drying Technology", *IEEE Transactions on Semiconductor Manufacturing* 2, 69–75.

Hall (1984) "Contamination Control of High Purity Water", *Semiconductor International*, 182–186.

Chylinski, et al. (1992) "Two–Parametric Method for Measuring the Radioactive Concentration of $^{22}$Na", *Nuclear Instruments and Methods in Physics Research* A312, 76–80.

Heydorn (1993) "Effect of Cascade Coincidences on the Efficiency Calibration of a Gamma–X Detector", *Journal of Radioanalytical and Nuclear Chemistry* 169, No. 2, 419–427.

Balazs (1987) "A Summary of New Methods for Measuring Contaminants in Ultrapure Water", *Microcontamination*, 35–40, and 62.

RADIONUCLIDE EXCHANGE DETECTION OF ULTRA TRACE IONIC IMPURITIES IN WATER

FIELD OF THE INVENTION

The present invention relates to an analytical method to monitor and detect trace elements in liquids, such as water.

BACKGROUND OF THE INVENTION

High purity water is required for many purposes, including use in pharmaceuticals, medicine and biology. Many industrial manufacturing processes require the use of ultra high pure water either as a direct process fluid or as the major component of a liquid product. This is particularly true of the pharmaceutical, electronic and electrical utilities industries. Purity of water used in the pharmaceutical industry is clearly required because of the health involvement in the final product. Greater and greater purity of water in the electronics industry is required due to the continually greater miniaturization in the manufacture of electronic devices on semiconductor substrates, such as single crystal silicon wafers. Impurities on the substrates in the region of the electronic device formation cause defects in the devices formed, which may considerably lower the yield of good products of the manufacturing process as well as affecting the long term reliability of the product manufactured.

For example, heavy metal impurities, such as copper, nickel, chromium and especially iron, in the crystal silicon wafers have adverse effects on the electrical properties thereof and on the yields of the integrated circuits formed therefrom. The actual effects of the heavy metal impurities on silicon electrical properties are varied, depending on the form that the impurity takes in the matrix of the silicon crystal. Metallic impurities which remain dissolved within the silicon matrix create mid-band gap trap centers which increase generation rate and ultimately result in increased current leakage of diffused junctions. In addition, heavy metal impurities can agglomerate and form separate and distinct metal-silicide precipitates. The effect becomes even more pronounced as the products become miniaturized, especially in the manufacture of ultra large scale integrated circuits.

Water is required in large quantities for rinsing semiconductor products after many steps in the production process and/or to remove contaminants from the silicon wafers. However, when water contains contaminants, especially metals, they will deposit on the silicon wafers, creating the aforementioned defects. To minimize contamination, the water utilized should be as pure as possible, and thus contain as little metal contaminants as possible. Therefore, ultrapure water is required in the processes.

It is important that once the water of ultrapure quantity is obtained, it remains ultrapure and does not become contaminated with metal contaminants. Unfortunately, quite often, the quality of the water deteriorates over time. This can occur in a variety of ways. To illustrate this, it is necessary to digress and generally outline the production of ultrapure water.

In the conventional production of ultrapure water, the starting water is passed through a pretreatment apparatus and a primary pure water production apparatus. The pretreatment apparatus and the primary water apparatus are ordinarily installed in a building apart from a factory building in which semi-conductor production apparatuses, for example, are installed. The primary pure water is introduced into a high purity water tank installed in a factory building via a primary pure water pipe.

The water stored in the water tank is passed through a subsystem wherein the water is treated and converted to ultrapure water. This ultrapure water is introduced into the semiconductor production apparatus via an ultrapure water pipe. The ultrapure water is continuously recirculated through a point just before the semiconductor production apparatus and in returned to the high purity tank via a return pipe. Thus, a loop is formed between the high purity water tank, the treatment subsystem, the ultrapure water pipe and return pipe, and the ultrapure water is circulated constantly through the loop.

It is known, however, in the above-described conventional arrangement, that the quality of the ultrapure water is reduced in its purity when it stops flowing and is stagnant. Contaminants, such as inorganic salts, especially metal containing inorganic salts contained in the pipe, etc. dissolve in the ultrapure water at the portion of the pipe, etc. contacting the ultrapure water. Therefore, the ultrapure water has to be circulated constantly in the loop to prevent deterioration of the purity of the ultrapure water.

However, the subsystem and the semiconductor production apparatuses are installed relatively far from each other. This arrangement necessitates the use of a long pipe for feeding the ultrapure water from the subsystem to the semiconductor apparatuses; the loop of the ultrapure water pipe reaches 100–500 meters in some cases. When ultrapure water is passed through a long pipe, the purity of the ultrapure water is reduced owing to, for example, the dissolution of impurities such as metal contaminants in the pipe. Further with the adoption of more complex semiconductor production steps and nondiversified semiconductor production apparatuses, the length of the ultrapure water pipe has become larger necessarily, which has resulted in a reduction in the quality of ultrapure water. In view of the trend towards higher density integration of circuitry used in semiconductors, it is important that the quality of the water introduced remains high. Therefore, the ultrapure water at its point of use needs to be monitored continuously to verity that the water is of sufficient quality. For example, in view of the adverse effects of the metal contaminants, it is important to monitor the water and verify that the concentration of the metal contaminants does not exceed tolerable levels.

Unfortunately, an adequate method of monitoring remains a challenge, especially at very low levels. The types of techniques utilized to date include, inter alia, Scanning Electron Microscopy, (SEM), particle counting tools, GC, FTIR, HPLC, ion chromatography, IR, UV, inductively coupled plasma (ICP), and atomic absorption. While SEM has become less expensive to implement and has excellent sensitivity, it requires effort, time and reasonable statistical models for use. Particle counting tools such as the Unizak model ERC 9320 counts particles from 0.3 to 0.05 micrometers in size in ultra pure water, but the results are not easily reproducible or interpretable. The other analytic methods, such as atomic absorption (AA), inductively-coupled plasma/mass spectrometry (ICP/MS) or X-ray fluorescence are impractical to implement as rapid, point of use monitors.

Therefore, it becomes important to find a methodology which is accurate, sensitive to metal or cation contaminants, provide reproducible results and can be utilized at point of use.

Moreover, it becomes imperative to find a methodology which would monitor the concentration of these cation contaminants at reasonable costs. To date, the only methodology available is the use of sensors for each individual cation that is suspected of being present in the system that is being monitored. This is quite expensive in and of itself. However, as the number of metals that are being monitored increases, the amount of equipment required also increases, and concomitantly therewith, so does the expense. Therefore, a methodology is desired that would monitor trace concentrations of metals more economically.

The present invention accomplishes these objectives and has these advantages.

More specifically, the present invention provides a way to monitor in real time at point of use the concentrations of a wide variety of trace impurities in the water. In utilizing the method of the present invention, it is possible to determine the amount of trace impurities in the water and to assess whether the water is of a sufficient purity for it to be utilized for its intended purpose. Furthermore the costs involved utilizing this method are significantly less than those associated with detecting trace cations heretofore.

SUMMARY OF THE INVENTION

The present invention is directed to the process for monitoring the total concentration of metal impurities in water at levels as low as ppb ("parts per billion") or even lower, at ppt ("parts per trillion"), which comprises passing a sample of water containing the metal impurities through an ion exchange resin containing a nuclide at a rate effective for sufficient contact between the ion exchange resin and the water to exchange the nuclide for the metal ions in the water, said nuclide being soluble in water, emitting gamma radiation, having a lower affinity for the ion exchange resin than the metals in the water, and having a half life sufficiently short to be detectable and sufficiently long to be practical, and (b) measuring the amount of the nuclide present in said water. This methodology is sensitive enough to detect such metals as iron ($Fe^{+2}$ and $Fe^{+3}$), copper ($Cu^+$ and $Cu^{2+}$), manganese (e.g. $Mn^{+4}$), magnesium ($Mg^{+2}$), aluminum ($Al^{+3}$) and the like in the trace concentrations indicated hereinabove.

DETAILED DESCRIPTION OF THE PREFERRED EMBODIMENT OF THE INVENTION

Figure 1:
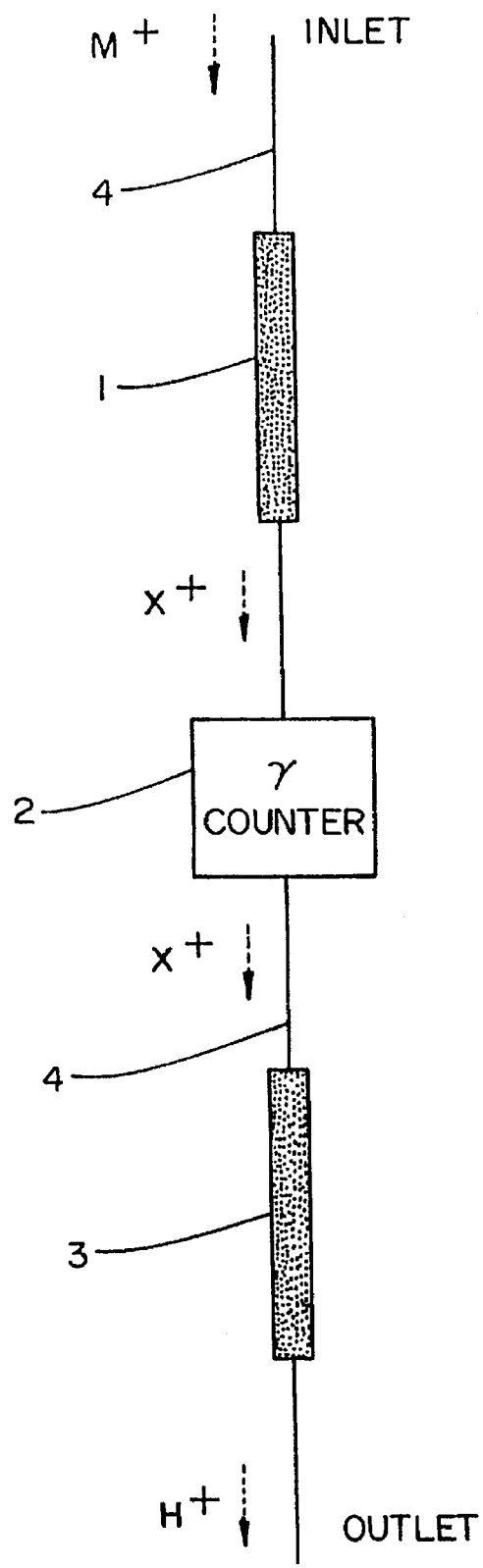
FIG. 1 schematically depicts the apparatus used in the present invention.

The present invention provides a quick and economical monitor at point of use of the overall concentration of metal impurities in water.

As indicated hereinabove, the water must contain as little metal contaminants as possible. Depending upon the purpose, the purity required may vary. Obviously the minimum level of purity required will be known to the person skilled in the art. The present invention is directed to monitor quickly at point of use the concentrations of a wide variety of metal contaminants.

Obviously, one means for making a determination of the level of metal impurities is to measure the concentration of each individual contaminant. However, this is time-consuming, and the determination of each metal contaminant, at point of use, is extremely difficult. In addition, the methodology is very expensive and as seen hereinbelow, unnecessary and wasteful of economic resources, in view of the methodology of the present invention.

However, a much more expedient and practical solution is accomplished by the present invention. It provides an overall total concentration of the metal contaminants present in the water. In this way, the skilled artisan utilizing the water obtains an appreciation of the purity thereof. If the total metal concentration is less than the threshold value, then the water has the requisite purity. If, on the other hand, the total metal contamination is above the threshold value, then the water may not be useable for the purpose intended and is either discarded or repurified and reanalyzed.

The present method provides a rapid, continuous assay for the total amount of exchangeable analyte without providing speciation. Such a method is preferred in manufacturing situations, for example, where sensitive real time monitoring of dissolved species bearing a broadly defined chemical functionality, e.g., metal ions, is more essential than precisely identifying each analyte. This technique is different from current techniques for off line operations which use exchange chemistry primarily to concentrate impurities but provide no way of coupling this to ultra-sensitive real time monitoring.

A further advantage of the present invention is that the costs involved for its implementation are significantly less than the costs associated with speciation, which require sensors for each individual component. For instance, less equipment and machinery is involved when utilizing the present invention; less experimental assays are required, and the equipment utilized in the present invention need not be as sophisticated.

Moreover, the present method is extremely sensitive. It can monitor trace metals in the water at concentrations as low as 100 ppq (100 parts per quadrillion) or lower. Thus, the present method can monitor the water for various metals when the metals are present in concentrations of 10 ppq or 100 ppt (parts per trillion) or less.

The analysis of the present invention is accomplished by utilizing an ion exchange resin containing a radioactive nuclide which exchanges with the metal impurities in the water and then detecting the nuclide in the eluted water.

The nuclide that is utilized in the present invention must have the following properties:

(1) It exchanges easily with the metal ions in the water. Obviously, the nuclide has an affinity for the cation exchange resin, but it has a lower affinity for the cation exchange resin than does the metal in the water. Thus, the nuclide replaces the metal in the water and is replaced by the metal on the cation exchange column. More precisely, the equilibrium constant for the exchange is large enough to favor displacement of the nuclide from the cation exchange resin in exchange for the metal impurity in the water.

(2) The nuclide is easily detectable utilizing standard radiological methods. More precisely, the nuclide is such that it can be detected at trace concentrations by conventional techniques known to one skilled in the art.

(3) The nuclide is soluble in water and readily dissolves in water.

(4) During the decay process of the nuclide, it or its decay products emit gamma radiation of such energy that the γ radiation can be detected by standard radiological techniques. Furthermore, the decay products are relatively stable elements, i.e., elements that are not strongly radioactive. Preferably, the nuclide decays into an element which is environmentally safe.

(5) The nuclide must have a long enough half life that it be practicable to utilize. Obviously, the half-life should be long enough that the necessity of replacement (assuming no depletion by metal exchange) of the ion exchange column not be onerous. If the half-life is too short, then the ion exchange resin containing the nuclide must be frequently prepared, thus making the use of the nuclide impractical. On the other hand, the half-life should not be too long; the longer the half-life, the weaker the $\gamma$ flux, and the more difficult to measure and/or detect. Therefore, to be practical, the nuclide utilized in the present invention has a half-life of at least about a year; however, the half life should be no longer than 40 years. It is preferable that the nuclide have a half-life between about 2 years and 30 years.

Figure 2:
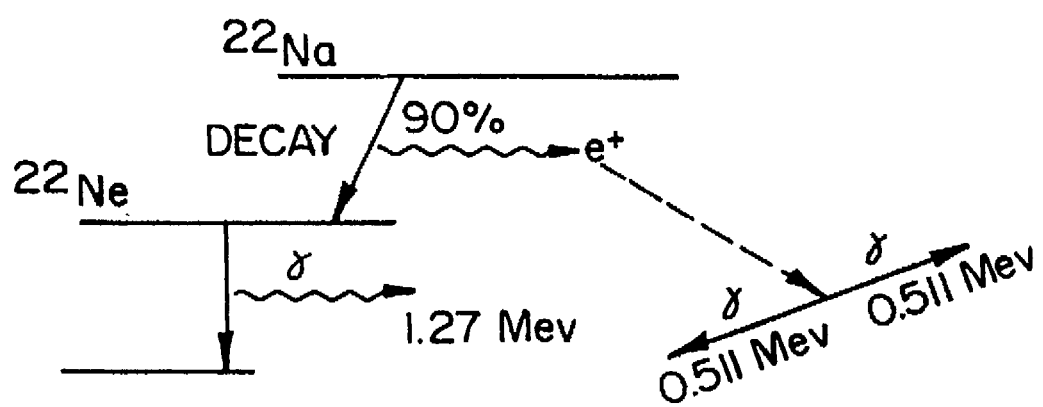
FIG. 2 is a sketch illustrating some of the nuclear radiation emitted by $^{22}Na$. Only one decay path is shown.

$^{22}$Na is an example of a nuclide which fits all of the aforementioned criteria. More specifically, it has a short half life of 2.6 years. The metal cation is exceedingly soluble in water. Further, it decays into an element of the periodic table that is stable and environmentally safe, i.e., $_{10}^{22}$Ne. During the decay, it emits $\gamma$ radiation which is easily detectable by known radiological techniques. FIG. 2 is a symbolic illustration of a portion of one path of the nuclear reaction of the decay of $^{22}$Na. $^{22}$Na decays to $^{22}$Ne by emitting over 90% of the time a positron and less than 10% of the time by electron capture. The position is annihilated in a very short time (a few nanoseconds) while emitting two gamma rays of the same energy, 0.511 MeV, and of opposed directions (i.e., 180 degrees apart). The $^{22}$Ne atom (resulting from the decay of $^{22}$Na) decays, in turn, by emitting a gamma ray of 1.27 MeV energy. All these events occur in a very short time, such as a few nanoseconds. Since the time interval is much shorter than the time resolution of the measuring devices, the two 0.511 MeV gamma rays are considered to be emitted simultaneously with the 1.27 MeV gamma rays. The $\gamma$ rays are of such intensity that they are easily detected by standard radiological methods, such as by a gamma counter.

Known detection methods can enhance the effective detection limit if the data is collected in a way that discriminates between random events and events in which there are observed effectively simultaneously emitted gamma photons, as described hereinabove.

Furthermore, $^{22}$Na exchanges easily with heavy metals on most cation exchange resins. As an indication of the lower affinity of sodium to cation exchange resins relative to the other metals, a general schematic of the retention of sample ions has been reported to increase in the following sequence of mobile phase counterions:

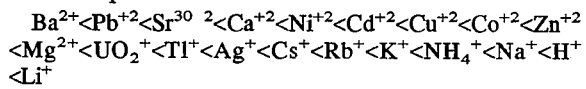

See Snyder and Kirkland, *Introduction to Modern Liquid Chromatography*, 2nd Ed. John Wiley and Sons, Inc. New York, N.Y., 1979, 410–452, 422 the contents of which are incorporated by reference. Although there is some variation in this schematic, depending upon the cation resin and the eluent, it generally describes the relative retention of the various metal ions to cation exchange resins. Thus, relative to the other metals, Na, in general, has a weaker affinity for binding to cations exchange resins.

Other examples of isotopes which also fit the criteria listed above include $^{60}$Co (half life of 5.27 years), $^{90}$Sr (half life of 28 years), $^{109}$Cd (half life of 1.3 years), $^{210}$Bi (half life of 22 years), $^{204}$Tl (half life of 3.9 years) and the like; however, these radionuclides present environmental issues, and are less preferred. Furthermore, as shown by the above schematic, these other metals exchange with fewer metals than $^{22}$Na and is to be utilized if the objective is to detect a more limited class of metals. Obviously, the choice of the metal nuclide utilized in the present invention is therefore dependent upon the particular circumstances. The most preferred isotopic nuclide is $^{22}$Na.

The nuclide used in the present invention is one element of the system that is used to monitor the water. The apparatus utilized in the present invention consists of other parts, as explained hereinbelow. An embodiment of the apparatus used in the present invention is schematically depicted in FIG. 1. Basically it consists of a vessel which includes a cation exchange medium containing the nuclide (1), such as $^{22}$Na, and a detector, e.g., a $\gamma$ counter (2), which is connected to the ion exchange medium by connecting means. The detector is positioned below the cation exchange medium. As the name suggests, the detector detects the presence of the radiation emitted from the nuclide. Optionally, the apparatus may contain a second cation exchange column (3) which is positioned below the detector and connected to the detector by connecting means and which contains a strongly acidic resin. These three elements are connected in succession using connecting means (4), such as plastic tubing, e.g., polyvinyl chloride, fluorinated tubing or piping and the like.

The water which is to be analyzed or a sample thereof is introduced via connecting means through an inlet of a column, reaction vessel or other physical containment which contains the cation exchange medium. The exchange medium consists of two parts—the (unexchangeable) support phase and the (exchangeable) nuclide, such as $^{22}$Na and the like.

When the water containing the trace metals contacts the exchangeable medium, a spontaneous chemical reaction occurs which results in the substitution of the analyte for the nuclide. Using X as the nuclide, for purposes of illustration, and $M^+$ for the trace metal in the solution, the reaction is characterized as follows: $M^+$ (soln)+$X^+$ (resin)$\rightarrow X^+$ (soln) +$M^+$ (resin)

Although $M^+$ is utilized in the above equation, it is to be understood that this does not mean that the metal in the water necessarily has a charge of +1. On the contrary, as used herein, the metal ion may have a charge (oxidation state) of +1, +2 or greater. For example, the $M^{3o}$ may be a Group IA metal, Group IIA metal, Group IIIA metal, transition metal, a lanthanide or actinide. Examples include $Fe^{+2}$, $Fe^{+3}$, $Cu^+$, $Cu^{+2}$, $Ni^{+2}$, $Mn^{+4}$, $Mg^{+2}$, $Al^{+3}$, $U^{+6}$, and the like.

As indicated hereinabove, the metal must have a greater affinity for the cation exchange resin than the nuclide. Put another way, the affinity of the nuclide for the cation exchange resin is very low so that it can be easily displaced by the metal ion. Thus, the equilibrium constant for the above reaction must be high enough to ensure that the resulting concentration of the nuclide-labeled species in the mobile fluid corresponds to the initial concentration of the analyte. The fluid which passes through and elutes from the column containing the exchange medium contains the single radiolabelled species at a concentration which is simply related to the sum total of concentrations of analytes in the fluid of interest. However, even metal cations which have equal or less affinity for the resin than $Na^+$ may catalyze an exchange as follows:

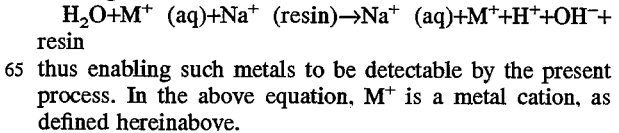

thus enabling such metals to be detectable by the present process. In the above equation, $M^+$ is a metal cation, as defined hereinabove.

As explained hereinbelow, there is approximate charge conservation so that the total charges exchanged (removed from the water and replaced by nuclide) remain constant. Thus, using sodium-22 as an example, for every monovalent metal cation removed from the water, it is replaced by one $^{22}$Na cation. Each divalent and trivalent metals in the water that is exchanged releases two or three sodium ions, respectively.

However, because of the complicated phase separation structure of the exchange medium, the charge will not always be fully conserved. Nevertheless, the data indicates that at least partial charged compensation occurs in the present system, which results in a significant increase in apparent recovery of the multiply-valent ions, as measured by the determined sodium in the eluent. In other words, by this technique, the results may tend to indicate a slightly higher metal concentration of trace metal elements than actually present in the water. This, however, is not critical. If the total metal concentration which is calculated in accordance with the method of the present invention is below the threshold values, then the skilled artisan is assured that the metal concentration in the water is below the threshold level. If, on the other hand, the total metal concentration calculated is at or above the threshold values, then the skilled artisan should discard, reanalyze, or repurify the water.

Various cation exchange resins can be utilized in the present invention.

The cation exchange resin used in the present invention are solid, unfractured structures. It preferably comprises as an essential component a synthetic organic polymeric matrix. It is preferably a sulphonated polystyrene crosslinked with a divinyl benzene. Alternatively, other combinations of exchangeable $^{22}$Na (or suitable nuclide) and phase separated or rigidly held chemical moiety with suitable metal affinity can be utilized, e.g, sol gel prepared powder incorporating crown ethers, cryptand, such as 18-C-6, or other cyclic or polycyclic organic structures.

Alternatively, inorganic resins such as zeolites, clays and other minerals with porous channels containing $Na^+$ or other alkali or alkaline earth counterions can be used as the exchange media. It will be recognized by those versed in the art that these structures afford the well-known property of size selectivity and therefore are capable of discriminating between different analytes based upon size. These materials may be natural minerals, such as zeolite X or Y, or they may be synthetic, i.e. man-made, such as ZSM-5 and ZSM-11. These examples are representative but by no means comprehensive. A further detailed account of the structures and the mechanisms of ion exchange for this group of materials may be found in Synthetic Zeolites, V1 and V2, Zhdunov, S. P.; Khvoshchev, S. S.; Feckitistova, N. N.; 1990, Gordon and Breach. Previous Pus. 1981, Khimiya Pub., Moscow; the contents of which are incorporated by reference.

Regardless of the type of cation exchange resin utilized, it is water permeable and can contact water with the exchangeable phase. Particle sizes of the ion exchange resin may vary, but they preferably range from about 0.1 microns to about 3 mm and more preferably, from about 25 microns to about 150 microns are suitable. Obviously, each cation exchange resin has different affinities for different metals. The cation exchange resin that should be selected is the one which has a high affinity for the trace metals in the water and has a much lower affinity for the nuclide. Preferably, the ratio of bonding affinity for the radionuclide to that of the metal contaminant is less than about 1, more preferably less than about 0.1 and most preferably less than about 0.001.

Various ion exchange resins that can be utilized include AMBERLITE® IRP-69, AMBERLITE® IRC-718, DUO-LITE® C467, AMBERLITE® GC-50, IRA-743, IR-118(H), IR-120, IRC-50S, IRP-64, AMBERLYST® 15, XN 1010, DOWEX® 50-H, Sulfonic Acid Resins, Perspective Biosystems PORUS® , S, HS, CM, and the like.

The flow rate of the water through the cation exchange resin should be sufficient to give the desired volume sampling rate, but slow enough to ensure exchange of trace metals that equilibrate with the exchange medium. Although the proper flow rate is dependent upon the type of cation exchange resin utilized and can easily be determined by one skilled in the art without undue experimentation, the preferred flow rate is between about 0.2 ml/min and about 10 ml/min and more preferably between about 1 and about 5 ml/min.

After the fluid is eluted from the cation exchange resin, the eluted fluid containing the nuclide species flows through a detector (2), which is instrumented for the ultra-sensitive detection of the nuclide in the water. The detector is a known type that is normally utilized by one skilled in the art for the detection of radioactive nuclides. More specifically, the detection of the radioactivity is accomplished by counting the gamma flux of the eluent and is measured in a gamma counter. It is preferred that the detector is attached to a recorder, so that the output of the detection is recorded by a recording device of a known type. The amount of radioactivity measured is compared with the values obtained from standard water containing known amounts of the nuclide. Thus, the nuclide concentration and therefore the concentration of metal contaminants can be calculated. Because the detection limit of the nuclide is independent of the detection limit for the analyte and independent of the number of different analytes, the sensitive radiochemical detection enables indirect continuous assay for the analytes of interest at ultra-trace levels.

These are the only two elements required in the present invention. However, a third element, which is optional, may also be a part of the apparatus. In a preferred embodiment, the present apparatus contains a second cation exchange column, which is connected to the detector. The second cation exchange column contains a strongly acidic exchange resin—the hydrogen form of the cation exchange resin used in the first column or more preferably, an exchange resin whose affinity is optimized for the removal of the nuclide, e.g., $Na^+$, from the liquid. The eluent from the detector passes into this column. The resulting nuclide for hydrogen exchange removes essentially all of the radioisotopic nuclide from the eluent, thus rendering the eluent suitable for discharge into a sewage waste treatment stream. The second cation exchange column may alternatively exchange other cationic species other than $H^+$ for $X^+$. In other cases, $M^{i+}$ is released into solution in exchange for $X^+$, wherein $M^{i+}$ is a metal cation which is relatively innocuous and in possession of some property which facilitates detection so that the lifetime of the second column can also be monitored, such as with a detecting device. The preferred embodiment incorporates $H^+$ as the cation released into solution. If necessary, the second exchange column resin can be removed periodically to dispose of the radionuclude waste. If the nuclide is $^{22}$Na, which has a short half life of 2.6 years, the radioactivity will have diminished to an insignificant level after approximately ten years (four half lives) and therefore, special precautions for removal thereof need not be taken. Alternatively, the collected $^{22}$Na can be recycled back to the cation exchange medium. The decay product of $^{22}$Na is the inert stable neon which is trivially disposed of.

In setting up the cation exchange column with the nuclide, for example, $^{22}$Na, the cation exchange resin should be treated initially.

In general, the cation exchange resin containing the radioactive nuclide is prepared by contacting the cation exchange resin with a salt solution containing the radionuclide dissolved in water. For example, if the radionuclide is $^{22}$Na, then the salt solution is a salt solution containing $^{22}$Na, such as $^{22}$NaNO$_3$, $^{22}$NaCl, and the like. The contacting may consist either of passing a solution containing the nuclide over the column of the cation exchange resin or by suspending the cation exchange resin in a solution of the nuclide. The pH of the solution is basic, i.e., the pH is slightly greater than 7, and more preferably in the range between 7 and 10. Although these methods of contacting are preferred, any other method of intimately contacting a solution containing the nuclide with the cation exchange material is suitable to permit equilibration thereof. The recommendations of the manufacturers of the ion exchange resins for the regeneration of the non-radioactive nuclide form, such as $^{23}$Na, of the exchange material would serve as a guide for optimal regeneration of a particular material. The amount of radioactivity bound to the cation exchange material, the duration of the contact time, and the ratio of the amount of nuclide present to the amount of cation exchange material as well as other conditions vary dependent upon the resin utilized, nevertheless, the appropriate parameters to be utilized is well known to the skilled artisan or is easily determined by simple experimentation.

The column is then prepared for use by flushing with ultrapure water until the eluent containing the nuclide approaches the asymptotic background limit.

The amount of radionuclide adsorbed onto the cation exchange resin can be determined and/or monitored utilizing radioactive detection techniques known to one skilled in the art, such as by utilizing a gamma counter. It is especially important to keep track of the nuclide concentration on the cation exchange resin. After packing the column with the desired exchange material, the resin is converted to the nuclide form, e.g., $^{22}$Na, by the techniques described hereinabove, such as passing the appropriate amount of the nuclide solution, e.g., the $^{22}$Na solution, through the column. Packing of the resin into the support container or column is a technique known to one skilled in the art. The amount of resin packed into the suitable support, container or column are typically that which is normally utilized in cation exchange chromatography. The set-up of the column with its radioactive nuclide is a technique which is easily practiced by one skilled in the art. For example, in an exchange experiment using unenriched exchange resin (IRP-69), approximately 3.93 meq. of Na is present in 1 gram of resin. This amount would obviously have to be considerably reduced for the experiment in which the radionuclide is incorporated, and the column chromatography would be carried out in a manner consistent with local, state, and federal licenses and guidelines. This would be accomplished by a combination of reducing the column size and proportions by an amount including, but not limited by factors, resulting in capillary dimensions. This would, depending on the application, also include but not be limited by an example where a column of 1 g of resin (from above) with an enrichment level of $1 \times 10^{-4}$ (0.01%) would have an activity of $5.17 \times 10^{-2}$ Ci. An enrichment level of $1 \times 10^{-6}$ would give a column having a gross activity of $5.17 \times 10^{-4}$ Ci (517 micro Ci), and so forth. The limiting factor in detection of the trace metals in every case is the column bleed level, which in the experimental configuration described herein was estimated at 1 ppb Na released into the eluent independently from the ion exchange process. Those versed in the art of ion exchange will appreciate that the bleed rate can be lowered through changes in the physical design of the apparatus, including but not limited, to lowering the column residence time. In summary, the appropriate combination of enrichment factor, column design, flow rate, shielding, and detector configuration would be chosen, depending on the application, and these are techniques known to the skilled artisan.

The water that is introduced through the inlet of the present apparatus and is monitored is a sample of the ultrapure water. Generally, it is a sample of the ultrapure water that flows through the ultrapure water pipe to its point of use. The present apparatus is connected to the ultrapure water pipe by connecting means at various points of the ultrapure water pipe, including at or in close proximity to its point of use.

In accordance with this preferred embodiment, one or more, actually any number permitted by the physical boundary available, sample collection lines or pipes run from each particular point in a pure liquid system for which one desires to have the quality of water monitored. However, at least one sample collection line runs from a point at or near the point of use, such as at the polishing (rinsing) stations. Another sample line may be connected at a point in the ultrapure water pipe at a point immediately after the point of use for diagnostic monitoring. The liquid flows through the ultrapure water pipe through valves located at the points wherein a sample line is connected to the ultrapure water pipe. These valves control the flow of the liquid to the apparatus of the present invention. When opened, a sample will flow through the sample flow line connecting the inlet of the apparatus to the ultrapure water pipe. The valve can be operated manually or if desired can be operated on a continuous desired cycle by use of a suitable programmed computer control system. Optionally, water way be pumped to the inlet of the apparatus of the present invention.

This invention finds particularity in the electronics industry both in the manufacture of semiconductor substrate materials, such as silicon, on which electronic devices are formed as well as in the electronic device houses where the electronic devices are formed on a silicon wafer. Both the silicon wafer and device processes are multistep and utilize ultrapure water at various steps in such processes. This invention is applicable for use in the pharmaceutical, electronic, and electrical utility industries. It is also for use in any industries where a continuous supply of ultrapure water is required for the processes involved. This would include liquids made from pure water such as parenterial solution and also food processing liquids.

To illustrate the feasibility of this invention, the following experiment was performed. It demonstrates the relationship between the metal concentration injected onto the column and the determined sodium concentration in the eluent. The following experiment shows that a given level of sodium ion in the eluent corresponds reliably to a given level of metal ion in the feed stream and that the calibration is roughly linear down to at least a background column bleed level. The bleed level is defined as the sodium concentration in the eluent when the input metal impurity level is virtually zero. This level will control the practical detection limit for trace metals in the sense that the detection limit scales are the square root of background counts. It is therefore important that the bleed be minimized by appropriate selection of flow rate and various physical parameters of the column.

Experiment

Experimental Details with Trace Metal Detection

The sodium nitrate (NANO$_3$ Baker Analyzed Reagent) and cupric nitrate (Cu (NO$_3$)$_2$. 3H$_2$O, Baker Analyzed Reagent) solution was used for the copper/sodium displacement experiment. The IRP-69 resin (R) Rohm and Haas, was purchased from Aldrich Chemical Company, Inc. All solutions were prepared using ultrapure demineralized water obtained from an in-house ultrafiltration system (Millipore Corp., Bedford, Mass.). This water was also used as a column eluent.

The displacement of sodium by copper was performed on a Dionex ion chromatographic unit. The flow rate was set at 1 mL per minute. The concentration of copper injected onto the column was verified by inductively coupled plasma spectrometry (ICP-AES) on an instrument SA model JY 38P (Edison, N.J.). Fractions of the eluent were collected using polyethylene tubes and analyzed for sodium using graphite furnace atomic absorption spectrometry (GF-AAS) on a Zeeman 4100 ZL atomic absorption spectrometer (Perkin Elmer Corp, Norwalk, Conn.).

The test column (0.3×24 cm) was prepared by packing with an aqueous slurry of the IRP-69 resin at atmospheric pressure. It was necessary to pretreat the resin with aqueous sodium carbonate in order to remove traces of acid sites which remove metal from solution without displacement of sodium.

Figure 3:
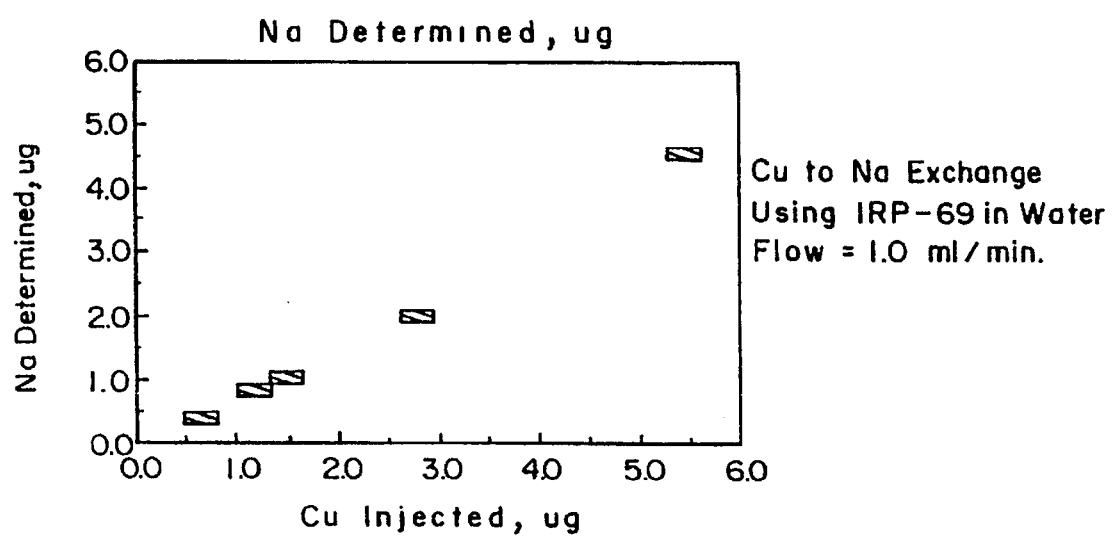
FIG. 3 is a graphical representation depicting the copper to sodium exchange in water using a IRP-69 ion exchange resin, with a flow of 1.0 ml/min.

The procedure used to establish quantitative exchange of a transition metal for sodium on the column was as follows:

Injections of 50 mL of copper solution at various concentrations were made onto the column with the flow rate steady at 1 mL per minute. The eluted ions were detected by solution conductivity changes and collected in tubes for quantitative analyses. In addition, several control samples were prepared: background column bleed, samples and standards of stock copper and sodium solution, and source ultrapure water samples. The relevant data are summarized in the table hereinbelow and plotted in FIG. 3. Four dilutions of the standard copper solution of 102.3 mg per liter were prepared and injected onto the column. Each injection produced a single sharp peak in the chromatogram and the collected fractions were analyzed by GF-AAS for sodium or by ICP-AES for copper. The column bleed level of sodium remained at about 20 µg per liter throughout the runs. This value was used to create the determined sodium values from the fraction collection and analyses. The data is tabulated hereinbelow:

TABLE

Cu-to-Na Exchange Data for IRP-69 Resin

| Solution | Calculated Concentration ($Cu^{+2}$) · mg/ml | Mass Injected ($Cu^+$) · µg | Mass Determined ($Na^+$) · µg | ($Na^+$) % Recovery |
|---|---|---|---|---|
| 1 | 102.3 | 5115 | 4390 | 84.3 |
| 2 | 51.15 | 2558 | 1970 | 106 |
| 3 | 25.58 | 1279 | 1020 | 110 |
| 4 | 20.46 | 1023 | 810 | 109 |
| 5 | 10.23 | 512 | 400 | 108 |

The results clearly show that, based upon the amount of copper injected from the prepared samples, the recovery of sodium ion in the eluent is essentially quantitative, based upon a copper to sodium ration of 1:2. Furthermore, the response of the system is essentially linear down to the column bleed limited sodium concentration under these conditions. Because the recovery of sodium is high, a shorter column can be used for the analysis, thus reducing the background without affecting the exchange efficacy. The ultrapure source water was found to have about 2 µg per liter of sodium.

Although the above description was limited to the detection of heavy metals in water, the present invention is not so limited. The techniques hereinabove are also applicable to detect metals in various other liquids especially organic liquids such as alcohols, e.g., methanol, ethanol, iso- or n-propanol, n-butanol, 2-butanol; organic solvents, such as N-methyl pyrrolidine, ethers such as tetrahydrofuran, para- or meta-dioxanes, polyethers; glycols, and the like as well as mixtures of the liquids (e.g. organic solvents) and water.

The methodology described herein not only detects trace metals in purified liquids, but also is applicable to detecting trace amounts of cations, whether it be organic or inorganic. By organic, it is meant to include aliphatic groups, aromatic groups, heterocyclic groups, and the like. More specifically, the technique is useful for detecting cations that would exchange with the nuclide, such as $^{22}Na$ and have a lower affinity for the cation exchange resin. Examples include alkyl-, alkylaryl-, hydroxyalkyl- or hydroxyalkylarylammonium ions, $NH^{+4}$, mono alkyl ammonium ions, dialkyl ammonium ions, trialkyl ammonium ions, tetraalkylammonium ions, and quaternary ammonium ions of all types, and the analogous phosphonium, arsonium and stibonium (or antinomium) analogs thereof and the oxonium, sulphonium and silenonium ions of analogous homologous descriptions. Examples include the quaternary ammonium ions of the following compounds: diethanolamine, methylaminoethanol, triethanolamine, 1-(dimethylamino-2-propanol), diethylaminoethanol, N-(n-proyl) diethylamine, ethanolamine, propylethanolamine, tetraphenylphosphonium, triethylsulfonium, and the like.

The alkyl and aryl groups described hereinabove have their normal meaning in organic chemistry, e.g. the alkyl group include cycloalkyl groups. Although as a theoretical matter, these alkyl and aryl groups have no upper limit, as a practical manner, it is rare that alkyl groups contain more than 26 carbons, and the aryl groups contain more than 26 ring carbon atoms. It is to be understood that the heterocyclic groups or heteroaionamatic groups may contain up to 10 heteroatoms on the ring. The heteroatoms are preferably O, S, N, or P, and the present methodology is capable of detecting the cation whether it appears on the ring or as a substituent on the ring.

These cations discussed hereinabove are normally impurities in the system that arise from chemical synthesis. For example, they may be impurities that were present in the reagents or solvent or that may have arisen as by-products in the synthesis itself. Even after the sample has been purified by techniques known to one skilled in the art, trace amounts thereof may still remain. Furthermore, it may be critical in a particular system that the cation impurities do not exceed a critical level, especially in the pharmaceutical, electronic, food and electrical utility industries. Using the techniques described hereinabove, the present invention is useful for monitoring cations in trace concentrations.

The above preferred embodiments and examples were given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

Having thus described our invention, what we claim as new, and desire to secure by Letters Patent is:

1. A process for monitoring the total concentration of ions of trace metals in a water sample containing a plurality of said metals comprising (a) passing the water sample containing the metal ions through a cation exchange column containing $^{22}$Na at a rate effective for sufficient contact between the cation exchange resin and the water to exchange the $^{22}$Na for the metal ions in the water, (b) detecting the $^{22}$Na in the water that is eluted from the ion exchange column and (c) determining the total metal ion concentration in the water from the amount of $^{22}$Na detected.

2. The process according to claim 1 wherein the trace metals are transition metals.

3. The process according to claim 1 wherein the trace metals in the water sample exchangeable with the $^{22}$Na are iron, copper, nickel, aluminum, calcium, magnesium, manganese, cobalt or lead.

4. The process according to claim 1 wherein the cation exchange resin is an organic polymeric matrix sulfonic acid resin, silica gel or sol gel powder, zeolite, clay or alumina.

5. The process according to claim 1 wherein the cation exchange resin is sulfonic acid resin, ZSM-5, ZSM-11, Zeolite X, Zeolite Y or silica gel or sol gel powder incorporating crown ethers or cryptand thereon.

6. The process according to claim 1 wherein metal ions in the water at concentrations as low as 10 ppq can be monitored.

7. The process according to claim 6 wherein metal ions in the water at concentrations as low as 100 ppq can be monitored.

8. The process according to claim 7 wherein metal ions in the water at concentrations as low as 100 ppt can be monitored.

9. The process according to claim 1 wherein the $^{22}$Na in the water is detected by a gamma detector.

10. The process according to claim 1 which additionally comprises passing the eluent water from the detector into a second ion exchange column containing an acidic exchange resin to replace the $^{22}$Na from the water with hydrogen ions.

11. A process for monitoring the total concentration of ions of trace metal in a water sample comprising (a) passing the water sample containing the trace metal ions through a cation exchange column containing a radioactive nuclide at a rate effective for sufficient contact between the cation exchange resin and water to exchange the nuclide for the metal ions in the water, said nuclide being soluble in water, having a lower affinity for the cation exchange resin than that of the metal ions in the water, having a half life of at least one year and less than 30 years, and having the capability of emitting radiation when undergoing decay, (b) detecting the nuclide that is eluted from the ion exchange column, and (c) determining the total trace metal ion concentration in the water from the amount of nuclide detected.

12. The process according to claim 11 wherein the nuclide is $^{22}$Na, $^{60}$Co, $^{90}$Sr, $^{109}$Cd, $^{210}$Bi or $^{204}$Tl.

13. The process according to claim 11 wherein the trace metal is iron, copper, nickel, aluminum, calcium, magnesium, cobalt, manganese, or lead.

14. The process according to claim 11 wherein the cation exchange resin is an organic polymeric matrix sulfonic acid resin, silica gel or sol gel powder, zeolite, clay or alumina.

15. The process according to claim 11 wherein the ion exchange resin is sulfonic acid resin, ZSM-5, ZSM-11, zeolite X, zeolite Y or silica gel or sol gel powder incorporating crown ethers or cryptand thereon.

16. The process according to claim 12 which additionally comprises passing the eluent water from the detector into a second ion exchange column containing an acidic exchange resin to replace the nuclide from the water with hydrogen ions.

17. The process according to claim 11 wherein the nuclide in the water is detected by a gamma detector.

18. In an integrated process for the commercial production of ultra large scale integrated circuits comprising semiconductor chips, including in the manufacturing line thereof, the step of utilizing ultrapure water flowing through an ultrapure water pipe to rinse the chips to remove contaminants therefrom, the improvement comprising incorporating into the manufacturing line an intermediate testing of the quality of the ultrapure water flowing through the ultrapure water pipe at the point of rinsing or immediately before the point of rinsing to minimize loss of circuits due to contamination resulting from metal ions in the ultrapure water, which testing comprises (a) passing a sample of the ultrapure water through a cation exchange resin containing $^{22}$Na at an effective rate for sufficient contact between the cation exchange resin and the water to exchange the $^{22}$Na for the metal ions that are present in the water, (b) detecting the $^{22}$Na in the water that is eluted from the cation exchange column, and (c) determining the total amount of metal ions present in the water from the amount of $^{22}$Na detected.

19. In a method for monitoring the quality of a purified fluid in a fluid purification system and/or in a distribution system loop utilizing said this purified fluid for the presence of contamination resulting from the presence of a plurality of cations in said purified fluid, the improvement comprising (a) continuously obtaining fluid samples at one or more selected points in said purification and distribution systems, (b) passing said samples through a cation exchange resin containing a nuclide adsorbed thereon at an effective rate for sufficient contact between the cation exchange resin and the purified fluid to exchange the nuclide for cations that are present in the purified fluid, said nuclide being soluble in water, having a lower affinity for the cation exchange resin than that of the cations in the sample of purified fluid, having a half life of at least one year and less than 30 years, and having the capability of emitting radiation when undergoing decay;

(c) detecting the nuclide in the purified fluid that is eluted from the cation exchange resin, and (d) determining the total amount of cations present in the purified fluid from the amount of nuclide detected.

20. The process according to claim 19 wherein the nuclide is $^{22}$Na.

21. A method for detecting trace amounts of a cation in a purified liquid sample comprising (a) passing said sample through a cation exchange column containing a nuclide adsorbed thereon at an effective rate for sufficient contact between the cation exchange resin and the purified liquid to exchange the nuclide for cation that has a higher affinity for the exchange resin than the nuclide, (b) then passing said nuclide containing liquid sample through a detector to detect the nuclide present in the liquid sample and (c) quantitatively determining the amount of cation present in the sample liquid from the amount of nuclide present.

22. The method according to claim 21 wherein the nuclide is $^{22}$Na.

* * * * *